United States Patent
Blom et al.

(10) Patent No.: US 8,269,178 B2
(45) Date of Patent: Sep. 18, 2012

(54) CAPACITIVE TYPE PROXIMITY SENSOR

(75) Inventors: Antonius Hermanus Maria Blom, Escharen (NL); Carsten Heinks, Nordhorn (DE); Ronald Jan Asjes, Valkenswaard (NL)

(73) Assignee: Koninklijke Philips Electronics NV, Eindhoven (NL)

( * ) Notice: Subject to any disclaimer, the term of this patent is extended or adjusted under 35 U.S.C. 154(b) by 60 days.

(21) Appl. No.: 12/746,928

(22) PCT Filed: Dec. 9, 2008

(86) PCT No.: PCT/IB2008/055162
§ 371 (c)(1),
(2), (4) Date: Jun. 9, 2010

(87) PCT Pub. No.: WO2009/074953
PCT Pub. Date: Jun. 18, 2009

(65) Prior Publication Data
US 2010/0264321 A1    Oct. 21, 2010

(30) Foreign Application Priority Data
Dec. 13, 2007 (EP) .................................. 07123184

(51) Int. Cl.
*G01T 1/164* (2006.01)
(52) U.S. Cl. ................. 250/363.04; 250/363.03
(58) Field of Classification Search ............. 250/363.04, 250/363.03
See application file for complete search history.

(56) References Cited

U.S. PATENT DOCUMENTS

| | | | |
|---|---|---|---|
| 5,651,044 A | 7/1997 | Klotz, Jr. et al. | |
| 5,726,581 A | 3/1998 | Vranish | |
| 6,408,051 B2 * | 6/2002 | Habraken et al. | 378/117 |
| 6,894,509 B2 | 5/2005 | Johnson et al. | |
| 2001/0031039 A1 | 10/2001 | Habraken et al. | |
| 2006/0097734 A1 * | 5/2006 | Roziere | 324/662 |

FOREIGN PATENT DOCUMENTS

| | | |
|---|---|---|
| EP | 1324364 A2 | 7/2003 |
| WO | 2004023067 A2 | 3/2004 |
| WO | 2006025000 A1 | 3/2006 |

* cited by examiner

*Primary Examiner* — Christine Sung

(57) ABSTRACT

It is provided a capacitive type proximity sensor, comprising a sensing electrode, whereas the sensing electrode has a surface with electroconductive areas 113 and not-electroconductive areas 117, whereas the sensor is adapted for measuring an electrical field 110, 112 between the sensing electrode and an object 109, 111. Further it is described an apparatus for medical x-ray diagnosis and/or x-ray therapy and/or nuclear diagnosis/therapy, e.g. SPECT, a system for medical x-ray diagnosis and/or x-ray therapy and/or nuclear diagnosis/therapy, e.g. SPECT, a method for avoiding collision between an apparatus for medical x-ray diagnosis and/or x-ray therapy and/or nuclear diagnosis/therapy, e.g. SPECT, and an object, a program element and a computer readable medium. It is disclosed a capacitance type proximity sensor whose sensitivity of approaching objects has an improved independence from the special geometry of the sensor itself.

13 Claims, 5 Drawing Sheets

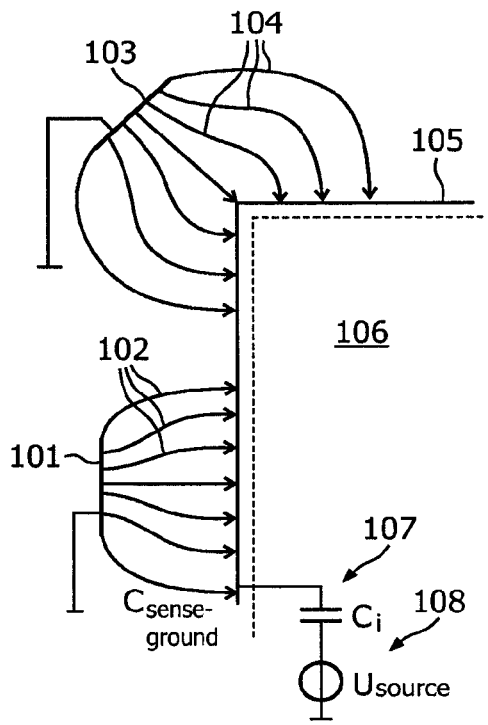
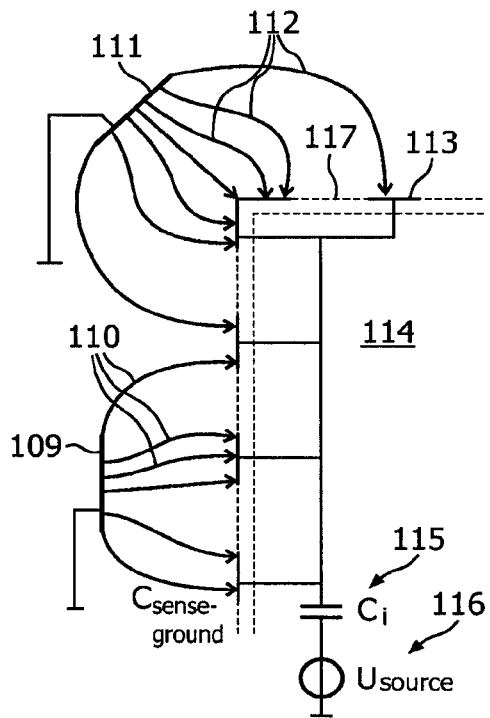
FIG. 1a (prior art)　　FIG. 1b
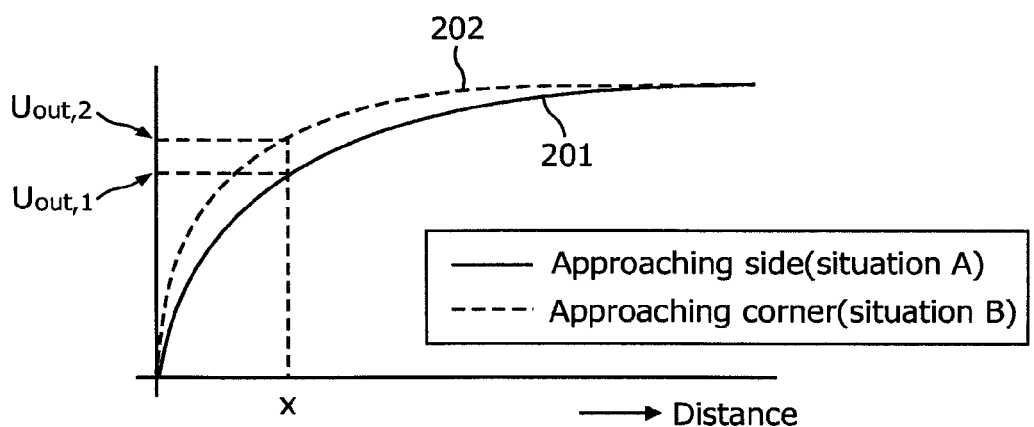
FIG. 2a

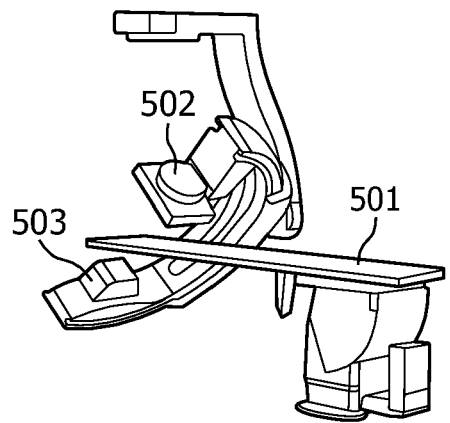 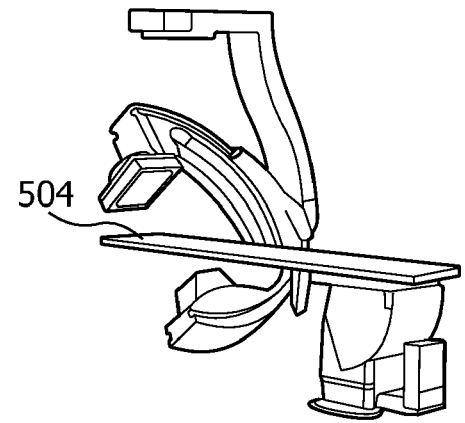
FIG. 5a  FIG. 5b
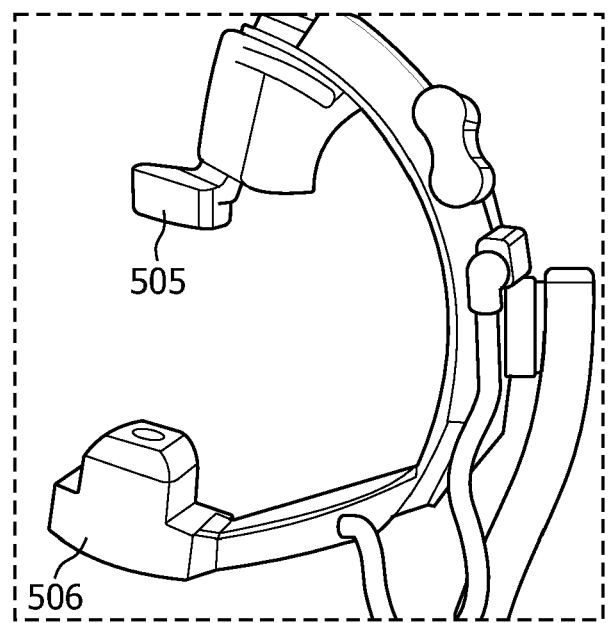
FIG. 5c

CAPACITIVE TYPE PROXIMITY SENSOR

FIELD OF THE INVENTION

The present invention relates to a capacitive type proximity sensor, an apparatus for medical x-ray diagnosis and/or x-ray therapy and/or nuclear diagnosis/therapy, e.g. SPECT, a system for medical x-ray diagnosis and/or x-ray therapy and/or nuclear diagnosis/therapy, e.g. SPECT, a method for avoiding collision between an apparatus for medical x-ray diagnosis and/or x-ray therapy and/or nuclear diagnosis/therapy, e.g. SPECT, and an object.

BACKGROUND OF THE INVENTION

Capacitive type proximity sensors are used intensively for distance detection purposes, featuring a flat, mostly round or square, sensing electrode. Guarding electrodes are used to obtain a linear measuring range, which is usually in the order of one-third of the sensor size. The same sensing technology is used for collision prevention purposes on Philips Medical equipment, featuring a measuring range which is larger than the sensor size.

The technique uses capacitive type proximity sensor electrodes along the outer boundaries of the casing of moving (Medical) equipment in order to detect the approaching of an object. In the first place it is meant as a preventive measure against colliding with the patient on the examination table and in the second place with other equipment in the direct environment.

The size and shape of the electrodes of the capacitive type proximity sensor are driven by the size and shape of the casing of the equipment. The sensing range of the detectors extends to distances which are even larger than the capacitive type proximity sensor structure itself. In such cases, the sensor characteristic will certainly not be linear with distance anymore.

A non linear characteristic is basically not a real problem as long as it reproduces nicely. Reproducing non-linear behaviour can only be expected when the sensor geometry remains fixed. The sensor geometry is basically configured by the shape of the two capacitive electrodes and their mutual distance and relative orientation. One electrode of the sensor is the surface of the object/target to be detected, and is thus not defined at all. The shape and size of the sensor electrode is driven by the shape and size of the equipment in question. In that way, there is a limited freedom in selection of sensor electrode shape and size. It is without question that the sensor characteristic shows significant variation, depending on object size and the relative position of the object to the shape of the sensor electrode. The result is that the collision prevention system comes up with stopping distances which vary significantly as well, depending on object size/shape and relative approaching position over the sensor electrode area.

In the present systems, the effective range of stopping distances is acceptable, when calibration steps are done. Sometimes small (mechanical) modifications or an ad-on is made in the sensitive area of the sensors, introducing extra variation. This step brings extra stopping distance change, needing an extra calibration step.

SUMMARY OF THE INVENTION

The consequently non-linear, reproducing, characteristic of the sensor is well accepted. The sensor characteristic only reproduces however, in case the sensor geometry remains the same. The sensor geometry comprises the sensor electrode shape on one hand and the position, shape and size of the (grounded) object/target to be detected. The size and shape of the object can not be affected and the shape of the sensing electrode is more or less determined by the shape of the casing of the equipment.

The invention introduces a structure of the sensing electrode along the casing surface, which is shaped for minimum variation of the sensor characteristic for the various sensing positions over the entire area of the sensitive area. This feature limits the variation in stopping distances of the anti collision system, depending on the situation (specific position on the equipment and object size). At the same time it allows small modifications to be made on the equipment which affect the sensor behaviour in a limited way, still resulting in acceptable stopping behaviour of the anti collision system.

The invention provides a capacitive type proximity sensor, comprising: a sensing electrode, whereas the sensing electrode has a surface with electroconductive areas and not-electroconductive areas, whereas the sensor is adapted for measuring an electrical field between the sensing electrode and an object.

The invention provides an apparatus for medical x-ray diagnosis and/or x-ray therapy and/or nuclear diagnosis/therapy, e.g. SPECT, comprising a sensor according to anyone of the claims 1 to 9. SPECT is a nuclear medicine tomographic imaging technique, whereas gamma rays are used. SPECT stands for Single Photon Emission Computed Tomography.

The invention provides a system for medical x-ray diagnosis and/or x-ray therapy and/or nuclear diagnosis/therapy, e.g. SPECT, comprising an apparatus for medical x-ray diagnosis and/or x-ray therapy and/or nuclear diagnosis/therapy, e.g. SPECT; and an object, whereas the object comprises a sensor according to anyone of the claims 1 to 9.

The invention provides a method for avoiding collision between an apparatus for medical x-ray diagnosis and/or x-ray therapy and/or nuclear diagnosis/therapy, e.g. SPECT, and an object, comprising: measuring the distance between a sensor according to anyone of the claims 1 to 9 and the object; and stopping an approaching between the apparatus and the sensor, if the distance is low, whereas the apparatus comprises the sensor.

The invention provides a programme element, which, when being executed by a processor, is adapted to carry out the method of claim 12.

The invention provides a computer readable medium having stored the programme element of claim 13.

Further embodiments are incorporated in the dependent claims.

According to an exemplary embodiment the sensor is provided, whereas the object is grounded.

According to a further aspect of the invention the sensor is provided, whereas the electroconductive areas are electrically connected.

According to a further aspect of the invention the sensor is provided, whereas the electroconductive areas are electrically connected to the processing electronics.

According to a further embodiment of the present invention the sensor is provided, whereas the surface has substantially flat regions and these substantially flat regions have not-electroconductive areas.

According to an exemplary embodiment the sensor is provided, whereas the surface has substantially non-flat regions and these substantially non-flat regions have electroconductive areas.

An exemplary aspect of an exemplary embodiment of the invention may be seen in that, the sensor is provided, whereas the conductive areas have dimensions which are optimised to the size of the overall sensing electrode dimensions, optimising the uniformity of the sensor sensitivity over the area of the whole structure.

According to a further aspect of the invention the sensor is provided, whereas the sensitivity of the sensor is substantially independent of the shape of the sensor.

According to a further embodiment of the present invention the sensor is provided, whereas the object is an animal or a human being.

It may be seen as a gist of the present invention to provide a capacitance type proximity sensor whose sensitivity of approaching objects is optimised with respect to independency from the special geometry of the sensor itself.

It should be noted that the following described exemplary embodiments of the invention apply also for the method, the device, the programme element and the computer readable medium.

It should be noted that the above features may also be combined. The combination of the above features may also lead to synergetic effects, even if not explicitly described in detail.

These and other aspects of the present invention will become apparent from and elucidated with reference to the embodiments described hereinafter.

BRIEF DESCRIPTION OF THE DRAWINGS

Exemplary embodiments of the present invention will be described in the following with reference to the following drawings.

FIG. 1a shows a closed surface sensing area of the sensing electrode;

FIG. 1b shows an open structure sensing area of the sensing electrode;

FIG. 2a shows a diagram of Uout dependent to the distance with the sensing electrode according FIG. 1a;

FIG. 5a shows a medical cardio-vascular product;

FIG. 5b shows the same medical cardio-vascular product in a different position;

FIG. 5c shows an other medical cardio-vascular product in greater detail;

DETAILED DESCRIPTION OF EXEMPLARY EMBODIMENTS

Figure 2B:
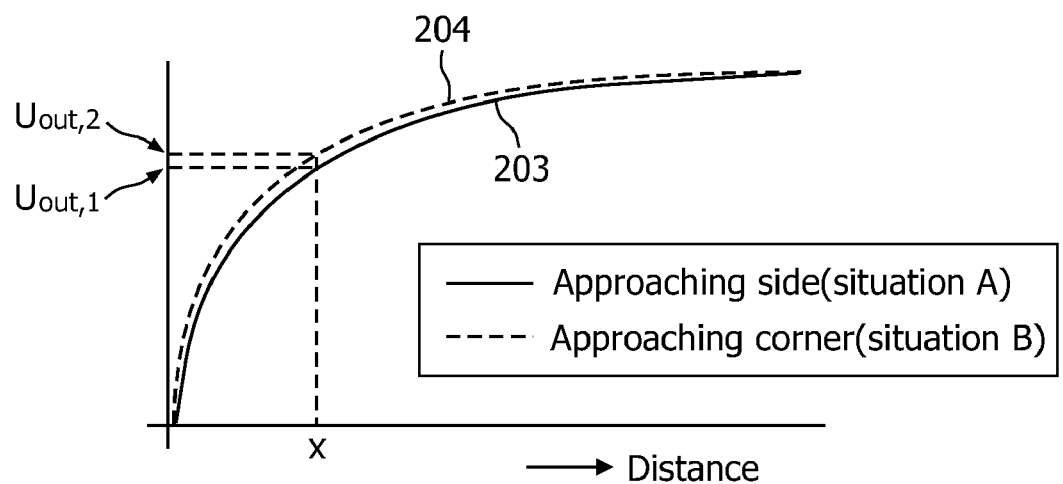
FIG. 2b shows a further diagram of Uout dependent to the distance with the sensing electrode according FIG. 1b.

The invention introduces a further structuring of the sensing electrode, affecting the sensor characteristics in such a way that the range of characteristics decreases. The range of sensor characteristics remains within a narrower band, leading to less variation in stopping distance.

The sensor electrodes of the collision prevention sensors have a 3-dimensional structure. The sensor sensitivity will be quite different at the edges and corners of the electrode compared to the sensitivity at the larger flat areas of the structure. The invention introduces changes to this behaviour by modifying the electrode structure specifically at the larger flat areas of the sensor electrodes. The main problem for the existing technique is that the sensitivity for objects approaching the sensor structure at the flat areas is significantly larger than for objects approaching the sensor at the corners or the edges. The invention uses a sensor electrode structure with the electrode maintained near the edges and corners, while it has an open structure at the flat areas. In this way, the sensitivity at the edges and corners will hardly be affected, while the sensitivity at the flat areas has decreased. The structuring of the sensor electrode results thus in a more balanced sensitivity over the entire sensor surface, leading to a more uniform stopping behaviour in terms of clearance distance after stopping.

Accepting a certain range of stopping distance, this approach allows more variation in sensor behaviour due to adaptations on the equipment. This feature is of prime importance for mounting an additional mechanical spacer on the cover of an X-ray source, forcing a minimum distance between X-ray source and human tissue. This additional unit is provided with sensor electrodes as well, having a rather low sensitivity figure due to the curved shape of the spacer. The technique of the invention comes up with acceptable stopping behaviour with and without the spacer, even without doing a calibration step after the spacer change.

FIG. 1a and FIG. 2a show in a simple arrangement the basic problem associated with the capacitive measuring technique for distance sensing where the sensor electrode structure has a complex three dimensional shape. FIG. 1a shows an object 106, which could be for example a casing of an X-ray source. On this casing there is a surface 105, which is electrically conductive. This surface 105 is the sensing electrode, which is connected with a voltage source, $U_{source}$, via an internal capacitor Ci. Opposite to the casing 106 and the sensing electrode 105 there are elements 101 and 103. These elements 101 and 103 are connected with ground. Between these elements 101 and 103 and the sensing electrode 105 there is a capacitance $C_{sense-ground}$. The index sense-ground describes, that the capacitance is between the sensing electrode 105 and the grounded elements 101 and 103. There are also electrical fields 102 and 104 between the elements 101 and 103 and the sensing electrode 105.

Structuring the electrode helps to achieve a more balanced behaviour for the various approaching directions. The FIG. 1b shows the same situation (with e.g. a casing 114) with the exception, that a sensing electrode has an open structure sensing area. The total sensor comprises several electroconductive areas 113 and several not-electroconductive areas 117. These parts of the sensing electrode are connected together via a capacitor Ci 115 with a voltage source $U_{source}$ 116. Opposite to the sensing electrode there are elements 109 or 111. Between these elements and the electroconductive areas 113 of the sensing electrode there are streamlines of the electrical field 110 or 112.

Approaching a capacitive 3-dimensional sensor electrode with a relatively large object at a flat side (situation A), will show a significantly higher sensitivity over a larger range, compared to approaching it at a corner (situation B). Particularly at a distance in the order of the geometry size of the object, this phenomenon will be most effective. For the application field of distance sensing for collision prevention, it is desired to have the least spread in sensor characteristics due to these effects, as this gives the least spread in stopping distances. It is evident that a certain effect has to be accepted, because there is always a certain effect present. The effect can be decreased however by structuring the sensing electrode at the 3-dimensional surface of the machine part in stead of having closed surfaces.

FIG. 2a depicts the output voltage $U_{out}$, which is dependent to the distance between an element 101 or 103 and the sensing electrode 105. This diagram shows the sensitivity of an approaching element 102 or 103 according the situation of FIG. 1. The graph 201 depicts the characteristic of an approaching element 101. The graph 202 depicts the characteristic of an approaching element 103. There is a distinct difference between the graphs 201 and 202. Therefore, at the same distance x there are different voltages $U_{out,1}$ and $U_{out,2}$. The element 101 generates a lower voltage $U_{out,1}$ than the element 103, which generates the higher voltage $U_{out,2}$. The difference between both voltages $U_{out,1}$ and $U_{out,2}$ corresponds to the measurement error.

FIG. 2b depicts the same characteristics for approaching elements 109 or 111, respectively. It can be seen that the error in measurement according to FIG. 2b (difference between $U_{out,1}$ and $U_{out,2}$) is now drastically reduced.

Figure 3:
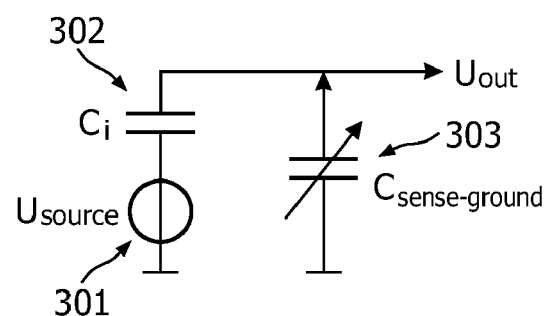
FIG. 3 shows a basic sensor readout circuit according both FIG. 1a or 1b.

FIG. 3 shows schematically the circuit according to the situations in FIG. 1a and FIG. 1b. The sensing electrode is connected to a voltage source $U_{source}$ 301 via an internal capacitor Ci 302. The electrical field between the elements 101, 103, 109 or 111, respectively, and the sensing electrodes lead to a capacitance $C_{sense-ground}$ 303. This capacitance $C_{sense-ground}$ 303 depends on the distance between the elements 101, 103, 109 or 111 and the sensing electrodes.

The described technique of structuring the sensing electrode for improved sensitivity uniformity has been applied on a collision prevention sensor on the X-ray tube cover of a Cardio-Vascular imaging system of Medical Systems in Best. The technique is essential in achieving a better stopping behaviour of the 'Bodyguard system' over the complete sensitive area of the cover. For a certain system, a set 402 of four sensors 401, 403, 404 and 406 is arranged in quadrants, inside the cover over the X-ray tube, having four full closed area sensor structures, shown in FIG. 4a. The four sensors 401, 403, 404 and 406 are separated by a non-electroconductive barrier 405. Implementing the structured electrode according the invention brings significantly less variation in stopping distance while providing at the same time a better sensitivity at the sensor electrodes of an optional spacer unit in front of the tube cover.

Figure 4A:
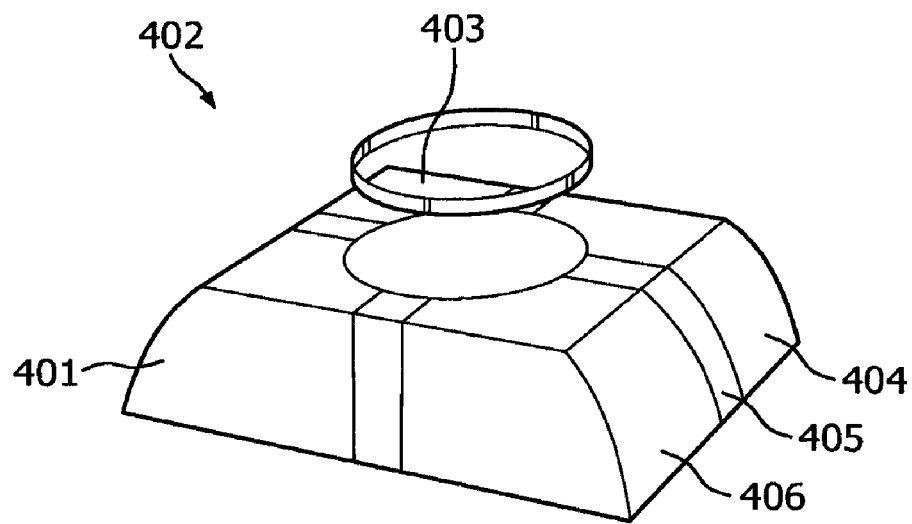
FIG. 4a shows 4 sensors with conventional sensing electrode with closed surfaces.
Figure 4B:
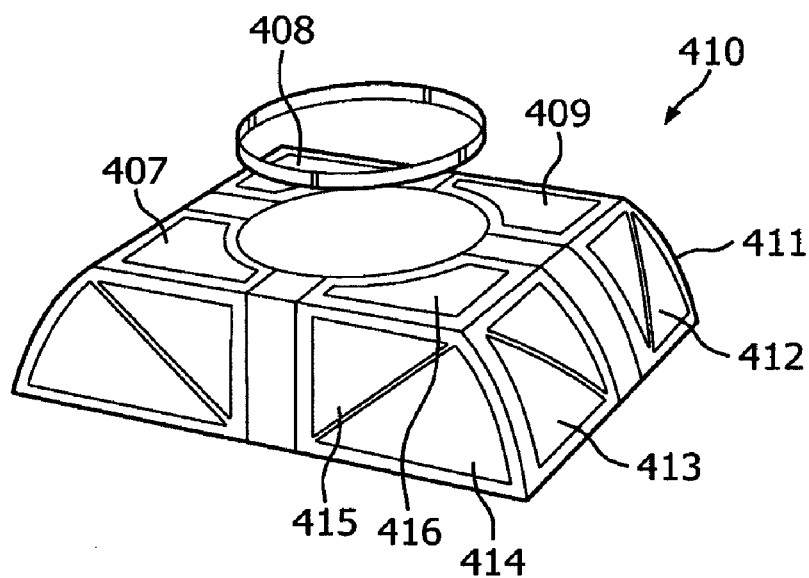
FIG. 4b shows 4 new sensors with new electrodes with open "skeletal" shaped structure for improved sensitivity uniformity over the entire sensor area.

FIG. 4b shows the same arrangement 410 but with the sensors according the invention. The sensors 407, 408, 409 and 413 have electroconductive areas 411 and 412 and non-electroconductive areas 414, 415 and 416. As mentioned in the previous paragraph, the sensor sensitivity of the (large) flat areas is decreased in favour of the lower sensitivity at the corners and edges by introducing openings in the sensor structure at these flat areas. FIGS. 4a and 4b show examples of a sensor electrode structure inside the cover of the X-ray tube of a Poly-G2 system. The basic electrode structure has been reduced from a full area conductive pattern (FIG. 4a), to a skeletal shaped pattern by limiting the conductive pattern to 10 mm wide stripes at each corner and edge 411. In addition to that, 5 mm wide diagonal stripes 412 have been added to the large openings to prevent that these areas come up with a too low local sensitivity.

Specific design tools will be developed to ease the design of successful electrode structures for a given application with its specific size and shape of casing on which the sensing functionality has to be designed.

Within the Philips Medical Systems division, several application are present for which the presented invention can upgrade its performance and for which it will be implemented in near future. These applications include systems from the Cardio Vascular group of X-ray imaging systems: PolyG2 tube cover, the tube cover for the Clea system and FD10 and FD20 X-ray detector units. FIGS. 5a, 5b and 5c show pictures of these system, with an indication of the position where the capacitive type proximity sensors for collision prevention have been implemented.

FIGS. 5a, 5b and 5c show a medical cardio-vascular product, whereas a patient table 501, 504 as well as a collision prevention sensor on detector casing 502, 505 and a collision prevention sensor on X-ray tube casing 503, 506 is depicted.

Apart from the Medical Systems area of applications, the technique is in general interesting for applications including robotic manipulation of equipment, where collision is an unwanted situation.

Application for the Philips Medical Systems Hamburg, General X-Ray Cardio Vascular BodyGuard: PMS Hamburg is a supplier of general X-ray systems to the medical industry. One of their new developments on X-ray systems is the Tango system. Within the Tango X-ray system a contactless object detection device will be part of the security concept. This device will prevent collision of the moving X-ray system with either persons or equipment inside the X-ray examination room. The Tango system consists of a patient-table and a detector ceiling suspension. The object detection system should provide proper (collision) data that can be interpreted by the motion control of the Tango system in order to avoid collision of parts of the system or the whole system especially with persons and as indication with furniture or other objects inside the X-ray examination room. By the interface the device provides data about the position of the detected objects in relations to the ceiling suspension or its parts in distance and direction.

Figure 6:
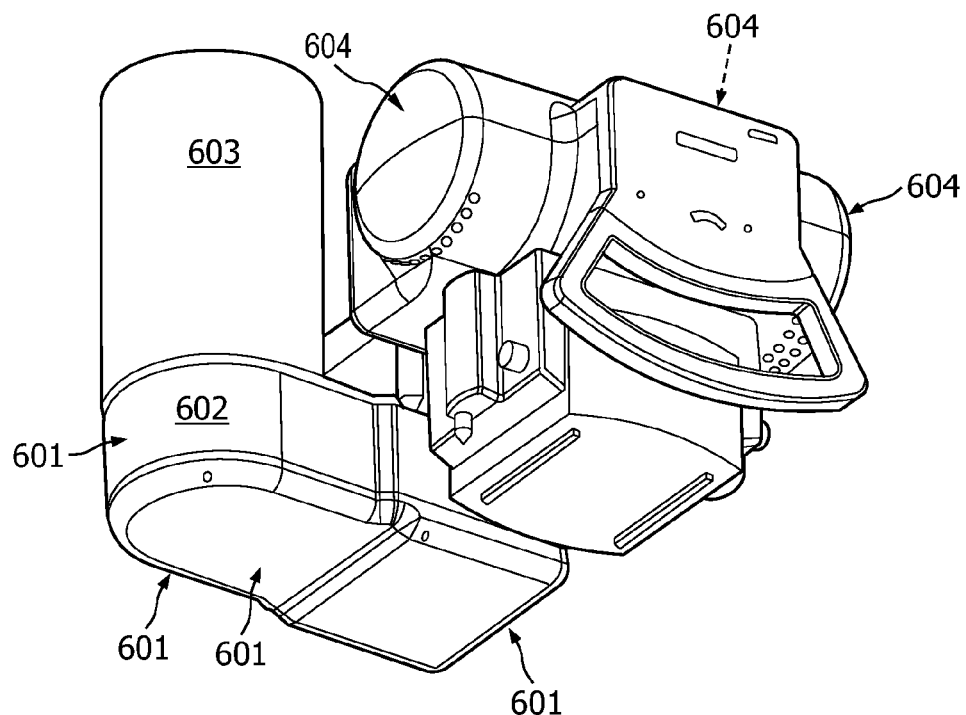
FIG. 6 shows an X-ray source with a ceiling suspension

FIG. 6 shows the detector ceiling suspension of the PMS Hamburg GXR Tango system. The different positions, where the "Capacity collision prevention sensors" are implemented are shown. FIG. 6 depicts a telescope 603, a swingarm 602, a sensors tube assembly 604 and a sensors swingarm 601.

Figure 7:
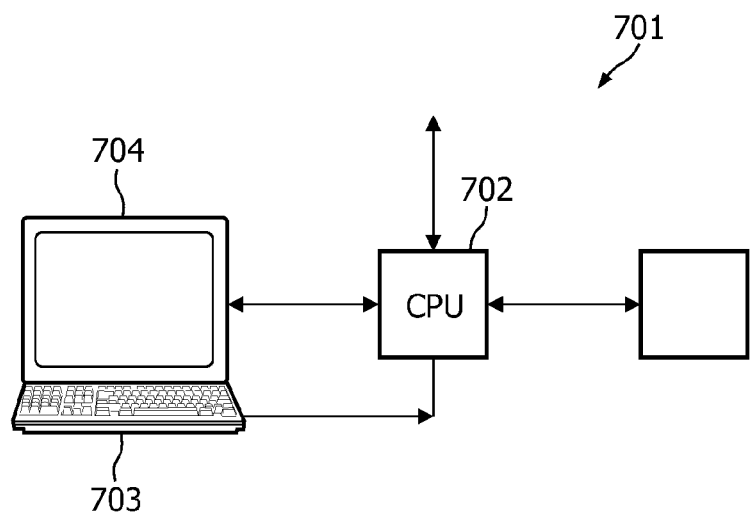

FIG. 7 shows a computer 701 on which a computer readable medium can be stored. The computer comprises a keyboard 703, a display 704 and an CPU 702.

It is provided a capacitive type proximity sensor, comprising a sensing electrode, whereas the sensing electrode has a surface with electroconductive areas 113 and not-electroconductive areas 117, whereas the sensor is adapted for measuring an electrical field 110, 112 between the sensing electrode and an object 109, 111. Further it is described an apparatus for medical x-ray diagnosis and/or x-ray therapy and/or nuclear diagnosis/therapy, e.g. SPECT, a system for medical x-ray diagnosis and/or x-ray therapy and/or nuclear diagnosis/therapy, e.g. SPECT, a method for avoiding collision between an apparatus for medical x-ray diagnosis and/or x-ray therapy and/or nuclear diagnosis/therapy, e.g. SPECT, and an object, a programme element and a computer readable medium. It is disclosed a capacitance type proximity sensor whose sensitivity of approaching objects shows improved independence from the special geometry of the sensor itself.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the internet or other wired or wireless telecommunication systems. Any reference signs in the claims should not be construed as limiting the scope.

LIST OF REFERENCE SIGNS 101 object (grounded)
102 streamlines of an electrical field
103 object (grounded)
104 streamlines of an electrical field
105 sensing electrode
106 cover
107 internal capacitance Ci
108 voltage source Usource
109 object (grounded)
110 streamlines of an electrical field
111 object (grounded)
112 streamlines of an electrical field
113 electroconductive area of the sensing electrode
114 cover
115 internal capacitance Ci
116 voltage source Usource
117 non-electroconductive area of the sensing electrode
201 graph of an object approaching the side of an sensing electrode
202 graph of an object approaching the corner of an sensing electrode
203 graph of an object approaching the side of an sensing electrode
204 graph of an object approaching the corner of an sensing electrode
301 voltage source Usource
302 internal capacitance Ci
303 variable Csense-ground (depends on the distance between object and sensing electrode)
401 sensing electrode
402 cover of an x-ray tube
403 sensing electrode
404 sensing electrode
405 non-electroconductive barrier
406 sensing electrode
407 sensing electrode
408 sensing electrode
409 sensing electrode
410 cover of an x-ray tube
411 electroconductive area of an sensing electrode
412 electroconductive area of an sensing electrode
413 sensing electrode
414 non-electroconductive area of an sensing electrode
415 non-electroconductive area of an sensing electrode
416 non-electroconductive area of an sensing electrode
501 patient table
502 collision prevention sensors on detector casing
503 collision prevention sensor on x-ray tube casing
504 patient table
505 collision prevention sensors on detector casing
506 collision prevention sensor on x-ray tube casing
601 sensors swingarm
602 swingarm
603 telescope
604 sensors tube assembly

The invention claimed is:

1. A capacitive proximity sensor, comprising:
a skeletal-shaped sensor electrode structure comprising an overall cupped or box-top shape;
a plurality of curved and straight conductive strips arranged as edges of a plurality of polygons, wherein the conductive strips connect the corners of the polygons, wherein the polygons lie in the surface of the overall cupped or box-top shape of the skeletal-shaped sensor electrode structure, and wherein the conductive strips define non-conductive openings within the polygons;
a plurality of conductive diagonal strips arranged to cross through the non-conductive openings within the polygons and connect opposing corners of the polygons;
wherein the capacitive proximity sensor is adapted for measuring an electrical field between the sensor electrode structure and an object.

2. The sensor according to claim 1, whereas the object is grounded.

3. The sensor according to claim 1, whereas the conductive strips are electrically connected.

4. The sensor according to claim 1, whereas the conductive strips are electrically connected to a circuit comprising a voltage source.

5. The sensor according to claim 1, wherein the conductive strips are ten millimeters in width.

6. The sensor according to claim 1, wherein the conductive diagonal strips are five millimeters in width.

7. The sensor according to claim 1, whereas the conductive strips have dimensions which are optimised to the size of the sensor electrode structure, optimising the uniformity of the sensor sensitivity over the area of the whole structure.

8. The sensor according to claim 1, whereas the sensitivity of the skeletal-shaped sensor electrode structure is substantially independent of its overall shape.

9. The sensor according to claim 1, whereas the object is an animal or a human being.

10. An apparatus for medical x-ray diagnosis, x-ray therapy, nuclear diagnosis, nuclear therapy, tomographic imaging, or computed tomography, comprising a sensor according to claim 1.

11. A method for avoiding collision between an apparatus for medical x-ray diagnosis, x-ray therapy, nuclear diagnosis, nuclear therapy, tomographic imaging, or computed tomography, and an object, the method comprising:
measuring the distance between a sensor according to claim 1 and the object; and
stopping an approaching between the apparatus and the object, if the distance is low, wherein the apparatus comprises the sensor.

12. A computer programmed to receive a signal from a sensor according to claim 1, and to carry out the steps of measuring the distance between the sensor and an object, and stopping an approaching between the apparatus and the object, if the distance is low, wherein the apparatus comprises the sensor.

13. A non-transitory tangible storage medium encoded with a machine readable computer program code, the code including instructions for causing a computer to implement a method for avoiding collision between an apparatus for medical x-ray diagnosis, x-ray therapy, nuclear diagnosis, nuclear therapy, tomographic imaging, or computed tomography and an object, the method comprising:
receiving a signal from a sensor according to claim 1;
measuring the distance between the sensor and an object; and
stopping an approaching between the apparatus and the object, if the distance is low, wherein the apparatus comprises the sensor.

* * * * *